United States Patent [19]
Hasegawa et al.

[11] Patent Number: 5,811,312
[45] Date of Patent: Sep. 22, 1998

[54] OPTICAL MEASUREMENT APPARATUS AND METHOD THEREFOR

[75] Inventors: Masanori Hasegawa; Tomoaki Ueda; Kazuhisa Shigemori; Kenji Masuda; Masakazu Yoshida; Tomomi Sakamoto, all of Kusatsu, Japan

[73] Assignee: Daikin Industries, Ltd., Osaka, Japan

[21] Appl. No.: 428,120

[22] PCT Filed: Aug. 30, 1994

[86] PCT No.: PCT/JP94/01431

§ 371 Date: Aug. 30, 1995

§ 102(e) Date: Aug. 30, 1995

[87] PCT Pub. No.: WO95/06872

PCT Pub. Date: Mar. 9, 1995

[30] Foreign Application Priority Data

Aug. 31, 1993 [JP] Japan ..................................... 5-215966
Apr. 18, 1994 [JP] Japan ..................................... 6-078998

[51] Int. Cl.⁶ .................................................. G01N 33/552
[52] U.S. Cl. .......................... 436/527; 356/317; 356/318; 385/12; 385/129; 385/130; 422/82.05; 422/82.08; 422/82.11; 435/287.1; 435/287.2; 435/288.7; 435/808; 436/535; 436/164; 436/165; 436/172; 436/805; 436/807
[58] Field of Search .............................. 385/12, 129, 130; 356/317, 318; 422/55, 58, 82.05, 82.08, 82.11; 435/287.1, 287.2, 288.7, 808; 436/527, 535, 164, 165, 172, 805, 807

[56] References Cited

U.S. PATENT DOCUMENTS

| | | | |
|---|---|---|---|
| 4,775,667 | 10/1988 | Saitoh et al. | 514/160 |
| 4,815,843 | 3/1989 | Tiefenthaler et al. | 356/128 |
| 5,039,490 | 8/1991 | Marsoner et al. | 422/82.01 |

FOREIGN PATENT DOCUMENTS

| | | |
|---|---|---|
| 61-226644 | 10/1986 | Japan . |
| 62-261036 | 11/1987 | Japan . |
| 62-503053 | 12/1987 | Japan . |
| 63-98548 | 4/1988 | Japan . |
| 225749 | 1/1990 | Japan . |
| 2167448 | 6/1990 | Japan . |

Primary Examiner—Christopher L. Chin
Attorney, Agent, or Firm—Beveridge, DeGrandi, Weilacher & Young, LLP

[57] ABSTRACT

An optical measurement apparatus includes a reaction vessel 2 which is formed in one body with a slab-type optical waveguide 1, and the apparatus adds fine-grains or water soluble dye for absorbing a fluorescent light which is radiated from fluorescent dye, and/or an exciting light so that stray light due to reagent is reduced and the S/N ratio of the optical measurement is improved.

45 Claims, 7 Drawing Sheets

OPTICAL MEASUREMENT APPARATUS AND METHOD THEREFOR

TECHNICAL FIELD

The present invention relates to an optical measurement apparatus and method therefor. More particularly, the invention relates to an optical measurement apparatus and method therefor which include a reaction vessel for housing a reagent liquid which includes fluorescent substance, and a test liquid for measurement so as to perform predetermined reaction. A casing constituted the reaction vessel, a part of which casing is formed of an optical waveguide. The apparatus and method measure optical characteristics in the vicinity of a surface of the optical waveguide, (the surface being a surface existing in the reaction vessel) by receiving a fluorescent light component. The fluorescent light component is output of a predetermined relative angle with respect to the optical waveguide due to the fluorescent substance, the fluorescent light being generated by radiating an exciting light into the optical waveguide at a predetermined relative angle with respect to the optical waveguide. Especially preferable, the present invention relates to an optical measurement apparatus and method therefor which excite a fluorescent substance constrained in the vicinity of a surface of an optical waveguide by an evanescent wave component. The evanecent wave component is generated by introducing an exciting light in the optical waveguide so as to propagate in a totally reflective manner. The invention measures the optical characteristics in the vicinity of the surface of the optical waveguide based upon a fluorescent light component which propagates within the optical waveguide in a totally reflective manner, including fluorescent light radiated from the fluorescent substance.

Background Art

In the past, an apparatus for measuring immunity using fluorescent light has been proposed which uses an optical measurement apparatus. The optical measurement apparatus excites a fluorescent substance constrained in the vicinity of a surface of an optical waveguide by an evanescent wave component. The evanescent wave component is generated by introducing an exciting light in the optical waveguide so as to propagate in a totally reflective manner. The optical measurement apparatus then measures optical characteristics in the vicinity of the surface of the optical waveguide based upon a fluorescent light component which propagates within the optical waveguide in a totally reflective manner, from fluorescent light radiated from the fluorescent substance.

Specifically, for example, a reaction vessel is provided which has a face united with a surface of a slab-type optical waveguide. Antibodies (or antigens) are previously fixed on the surface, and a test liquid for measurement and antibodies labeled with fluorescent dye (hereinafter, referred to as labeled antibodies) are poured within the reaction vessel in this order. Then, the labeled antibodies are constrained in the vicinity of the surface by an antigen-antibody reaction. The quantity of the constrained labeled antibodies corresponding to a concentration of antigens in the test liquid for measurement.

The fluorescent dye of the constrained labeled antibodies are excited by an evanescent wave component of the exciting light. The concentration of antigens in the test liquid for measurement is detected based upon an intensity of fluorescent light which is radiated from the fluorescent dye, propagated within the slab-type optical waveguide, and output from the slab-type optical waveguide.

Further, an apparatus for measuring immunity using fluorescent light is conventionally proposed which forms a reaction vessel on one side of an optical waveguide. An immunity reaction is performed between ligands which are made to be a solid phase on the surface of the optical waveguide, a test liquid for measurement which is pored within the reaction vessel, and ligands which are poured within the reaction vessel and which are labeled with a fluorescent dye. The apparatus excites the fluorescent dye by introducing a plane wave into the reaction vessel through the optical waveguide, and measures a degree of the immunity reaction based upon a component which propagates within the optical waveguide in a totally reflective manner from the fluorescent light radiated from the fluorescent dye (refer to Japanese patent laid open gazette of patent application publication No. Sho 61-502418). In this application, "ligand" means antigens, antibodies, hapten, hormones, or any organic substance which causes a specific bonding reaction.

Therefore, the fluorescent dye of the labeled antibodies within the reaction vessel are excited by an exciting light. And, a degree of immunity reaction is detected based upon an intensity of fluorescent light which is propagated within the optical waveguide by evanescent wave coupling and is output from the optical waveguide, including fluorescent light radiated from the fluorescent dye.

In the former apparatus for measuring immunity using fluorescent light, when the surface of the optical waveguide has a perfectly smooth face only fluorescence dye which is constrained in the vicinity of the surface by antigen-antibody reaction radiates fluorescent light. Also, fluorescence dye which labels unreacted antibodies never radiates fluorescent light. However, in actuality it is almost impossible for the surface of the optical waveguide to be made to have a perfectly smooth face. Therefore, not only, the evanescent wave component but also scattered component of the exciting light excite the fluorescent dye, so that fluorescent dye which labels unreacted antibodies also radiate fluorescent light. And, the fluorescent light radiated from the fluorescent dye constrained in the vicinity of the surface of the optical waveguide and the fluorescent light radiated from the fluorescence dye of unreacted labeled antibodies (hereinafter, referred to as stray light) are almost impossible to be optically separated from one another. Also, the stray light is easily varied by extrinsic factors such as temperature and the like. Therefore, a sensitivity of immunity measurement using fluorescent light is not improved too much.

To remove these the disadvantages, an operational processing may be carried out for separating a signal due to the stray light and a signal due to the actual reaction (hereinafter, referred to as a real signal) from one another. Disadvantages arise in that this operation is remarkably complicated, and data processing of the measurement timing becomes remarkably complicated, and it is not guaranteed that a sufficient measurement accuracy is obtained.

Further, the stray light is reduced when the intensity of the exciting light is lowered, but, a S/N ratio cannot be improved because the real signal becomes small simultaneously.

In the latter apparatus for measuring an immunity reaction using fluorescent light, not only the fluorescent dye which is constrained in the vicinity of the optical waveguide by immunity reaction, but also the unreacted fluorescent dye which has not participated in immunity reaction are excited by the exciting light. Further, fluorescent light which is radiated from the unreacted fluorescent dye is radiated through a transparent wall of the reaction vessel, and is detected by an optical detector together with signal light which propagates in the optical waveguide in a totally reflective manner. The above fluorescent light due to the unreacted fluorescent dye is remarkably difficult to separate from the fluorescent light due to the fluorescent dye which contribute immunity reaction. The above fluorescent light due to the unreacted fluorescent dye is also easily varied by the influence of extrinsic factor such as temperature and the like. Therefore, measurement sensitivity is remarkably impeded.

Further, to prevent the fluorescent light due to the unreacted fluorescent dye from being detected by the optical detector, it may be thought that a plate or the like for screening light which posses through a side wall of the reaction vessel and which light is not due to essential immunity reaction, with respect to the optical detector, is provided on the reaction vessel at an optical-detector-ward side thereof. Another disadvantage arises in that an arrangement of this type is complicated.

Disclosure of the Invention

The present invention was made in view of the above problems.

It is an object of the present invention to offer an optical measurement apparatus and method therefor which reduce a total quantity of fluorescent light which is radiated from unreacted fluorescent substances, so as to improve measurement sensitivity. Especially, it is another object of the present invention to offer an optical measurement apparatus and method which reduce stray light without influencing the real signal, so that a S/N rate of the optical measurement is improved.

To perform the above object, an optical measurement apparatus according to one embodiment of the invention is an apparatus which excites a fluorescent substance which is constrained in the vicinity of a surface of an optical waveguide. The fluorescent substance is excited by an evanescent wave component generated by introducing an exciting light so that the exciting light propagates within the optical waveguide in a totally reflective manner. The apparatus measures optical characteristics in the vicinity of the surface of the optical waveguide based upon the fluorescent light component which propagates within the optical waveguide in a reflective manner, from the fluorescent light which is radiated by the fluorescent substance. The apparatus includes fine grains which are added into the reaction vessel and which absorb light having at least one wavelength among an exciting wavelength of the fluorescent substance and an emitting wavelength of the fluorescent substance.

The apparatus excites a fluorescent substance which is constrained in the vicinity of a surface of an optical waveguide, by an evanescent wave component which is generated by introducing an exciting light so that the exciting light propagates within the optical waveguide in a totally reflective manner. The apparatus measures the optical characteristics in the vicinity of the surface of the optical waveguide based upon a fluorescent light component which propagates within the optical waveguide in a reflective manner, from includes fluorescent light which is radiated from the fluorescent substance. When the above measurement is performed, the apparatus comprises fine-grains which are added into the reaction vessel, and which fine-grains absorb light of at least one wavelength among an exciting wavelength of the fluorescent substance and an emitting wavelength of the fluorescent substance. Thus the apparatus can prevent the fluorescent substance from being excited by scattering of the exciting light which is generated at the surface of the optical waveguide, which fluorescent substance is not constrained in the vicinity of the surface of the optical waveguide. Also the apparatus can prevent the fluorescent light which is radiated from the fluorescent substance, excited by the scattered exciting light which is generated at the surface of the optical waveguide from being introduced into the optical waveguide. Therefore, the apparatus improves the S/N ratio of optical measurement.

An optical measurement apparatus according to a second embodiment of the invention is an apparatus which excites a fluorescent substance which is constrained in the vicinity of a surface of an optical waveguide. The fluorescent substance is excited by an evanescent wave component which is generated by introducing an exciting light so that the exciting light propagates within the optical waveguide in a totally reflective manner. The apparatus measures optical characteristics in the vicinity of the surface of the optical waveguide based upon the fluorescent light component which propagates within the optical waveguide in a reflective manner, from the fluorescent light radiated from the fluorescent substance. The apparatus comprises a water soluble dye which is added into the reaction vessel which absorbs light of at least one wavelength among an exciting wavelength of the fluorescent substance and an emitting wavelength of the fluorescent substance.

That is, the apparatus excites a fluorescent substance which is constrained in the vicinity of a surface of an optical waveguide. The fluorescent substance is excited by an evanescent wave component which is generated by introducing an exciting light so that the exciting light propagates within the optical waveguide in a totally reflective manner. The apparatus measures optical characteristics in the vicinity of the surface of the optical waveguide based upon a fluorescent light component which propagates within the optical waveguide in a reflective manner, from the fluorescent light which is radiated by the fluorescent substance. When the above measurement is performed, the apparatus comprises a water soluble dye which is added in the reaction vessel and which absorbs light of at least one wavelength among an exciting wavelength of the fluorescent substance and an emitting wavelength of the fluorescent substance. The apparatus can thus prevent the fluorescent substance from being excited by scattering of the exciting light which is generated at the surface of the optical waveguide, which fluorescent substance is not constrained in the vicinity of the surface of the optical waveguide. Also the apparatus can prevent the fluorescent light which is radiated from the fluorescent substance from being introduced into the optical waveguide, which fluorescent substance is excited by the scattered exciting light generated at the surface of the optical waveguide. Therefore, the apparatus improves the S/N ratio of optical measurement.

An optical measurement apparatus according to a third embodiment of the invention includes a reaction vessel in which a reagent, including a fluorescent substance, and a test liquid for measurement are housed so as to perform predetermined reaction. The apparatus includes a casing which constitutes the reaction vessel and a part which is constituted by an optical waveguide. The apparatus radiates an exciting light into the optical waveguide at a predetermined relative angle with respect to the optical waveguide, and measures optical characteristics in the vicinity of the surface of the optical waveguide which vicinity is within the reaction vessel. The measurement is performed by receiving a fluorescent light component from fluorescent light of the fluorescent substance, which component is output at a predetermined relative angle with respect to the optical waveguide. The apparatus comprises a substance which is added in the reaction vessel and which absorbs light of at least one wavelength among an exciting wavelength of the fluorescent substance and an emitting wavelength of the fluorescent substance.

That is, the apparatus includes a reaction vessel in which a reagent, including a fluorescent substance, and a test liquid for measurement are housed so as to perform a predetermined reaction. The apparatus has a casing which constitutes the reaction vessel and a part which is constituted by an optical waveguide. The apparatus radiates an exciting light to the optical waveguide at a predetermined relative angle with respect to the optical waveguide. The apparatus then measures, the optical characteristics in the vicinity of the surface of the optical waveguide within the reaction vessel, by receiving a fluorescent light component from the fluorescent light produced by the fluorescent substance. The fluoresent light component is output at a predetermined relative angle with respect to the optical waveguide. When the measurement is performed, the apparatus adds the substance in the reaction vessel. The substance absorb light which has at least one wavelength among an exciting wavelength of the fluorescent substance and an emitting wavelength of the fluorescent substance. The apparatus can thus prevent the fluorescent substance from being excited by scattering of the exciting light which is generated at the surface of the optical waveguide, which fluorescent substance is not constrained in the vicinity of the surface of the optical waveguide. Also the apparatus can prevent the fluorescent light which is radiated from the fluorescent substance from being introduced into the optical waveguide, which fluorescent substance is excited by the scattered exciting light which is generated at the surface of the optical waveguide. Therefore, the apparatus improves the S/N ratio of optical measurement.

An optical measurement apparatus according to a fourth embodiment of the invention is an apparatus which employs an optical measurement apparatus which introduces an exciting light into a reaction vessel through an optical waveguide so as to excite a fluorescent substance. The apparatus measures the optical characteristics in the vicinity of a surface of the optical waveguide based upon a fluorescent light component from the fluorescent light radiated by the fluorescent substance. This component propagates within the optical waveguide in a reflective manner.

The apparatus introduces an exciting light into the reaction vessel through the optical waveguide so as to excite the fluorescent substance, and then measures the optical characteristics in the vicinity of the surface of the optical waveguide based upon the fluorescent light component from the fluorescent light radiated by the fluorescent substance. The component propagates within the optical waveguide in a reflective manner. When the optical measurement is performed, the apparatus adds the substance in the reaction vessel which absorbs light having at least one wavelength among an exciting wavelength of the fluorescent substance and an emitting wavelength of the fluorescent substance. The apparatus prevents the fluorescent substance not constrained in the vicinity of the surface of the optical waveguide from being excited by scattering of the exciting light which is generated at the surface of the optical waveguide. Also, the apparatus prevents the fluorescent light which is radiated from the fluorescent substance from being introduced into the optical waveguide, which fluorescent substance are excited by the scattered exciting light which is generated at the surface of the optical waveguide. Therefore, the apparatus improves the S/N ratio of optical measurement. Further, the apparatus simplifies an arrangement of an optical system because an optical element is not necessary to separate the exciting light and the fluorecent light from one another.

An optical measurement apparatus according to a fifth embodiment of the invention employs an optical measurement apparatus which excites a fluorescent substance which is constrained in the vicinity of a surface of an optical waveguide, by an evanescent wave component which is generated by introducing an exciting light. The exciting light propagates within the optical waveguide in a totally reflective manner, and the apparatus measures the optical characteristics in the vicinity of the surface of the optical waveguide based upon a fluorescent light component which is radiated outward through the optical waveguide, from the fluorescent light radiated by the fluorescent substance.

The apparatus excites a fluorescent substance which is constrained in the vicinity of the surface of the optical waveguide, by the evanescent wave component generated by introducing the exciting light so that the exciting light propagates within the optical waveguide in a totally reflective manner. The apparatus measures the optical characteristics in the vicinity of the surface of the optical waveguide based upon the fluorescent light component radiated outward through the optical waveguide, from the fluorescent light radiated by the fluorescent substance. When the measurement is performed, the apparatus adds the substance in the reaction vessel, which substance absorbs light which has at least one wavelength among an exciting wavelength of the fluorescent substance and an emitting wavelength of the fluorescent substance. The apparatus can prevent the fluorescent substance from being excited by scattering of the exciting light generated at the surface of the optical waveguide, which fluorescent substance is not constrained in the vicinity of the surface of the optical waveguide. Also the apparatus can prevent the fluorescent light which is radiated from the fluorescent substance from being introduced into the optical waveguide, which fluorescent substance is excited by the scattered exciting light generated at the surface of the optical waveguide. Therefore, the apparatus improves the S/N ratio of an optical measurement. Further, the apparatus simplifies an arrangement of an optical system because an optical element is not necessary to separate the exciting light and the fluorescent light from one another.

An optical measurement apparatus according to another embodiment of the invention employs an optical measurement apparatus which excites a fluorescent substance which is constrained in the vicinity of a surface of an optical waveguide. An exciting light is introduced into a reaction vessel through the optical waveguide at a predetermined angle. The apparatus then measures the optical characteristics in the vicinity of the surface of the optical waveguide based upon a fluorescent light component which is radiated outward through the optical waveguide, from the fluorescent light radiated by the fluorescent substance. The component is output through the optical waveguide at an angle which is different from that of the exciting light.

That is, this optical measurement apparatus excites a fluorescent substance which is constrained in the vicinity of the surface of the optical waveguide, by introducing an exciting light into the reaction vessel through the optical waveguide at a predetermined angle. The apparatus measures the optical characteristics in the vicinity of the surface of the optical waveguide based upon the fluorescent light component which is radiated outward through the optical waveguide, from the fluorescent light radiated by the fluorescent substance. The fluorescent light component is output through the optical waveguide at an angle which is different from that of the exciting light. When the measurement is performed, the apparatus adds a substance in the reaction vessel which absorbs light having at least one wavelength among an exciting wavelength of the fluorescent substance and an emitting wavelength of the fluorescent substance. The apparatus can thereby prevent the fluorescent substance from being excited by scattering of the exciting light generated at the surface of the optical waveguide, which fluorescent substance is not constrained in the vicinity of the surface of the optical waveguide. Also the apparatus can prevent the fluorescent light radiated from the fluorescent substance from being introduced into the optical waveguide, which fluorescent substance is excited by the scattered exciting light generated at the surface of the optical waveguide. Therefore, the apparatus improves the S/N ratio of the optical measurement. Further, the apparatus simplifies an arrangement of the optical system because an optical element is not necessary to separate the exciting light and the fluorecent light from one another.

An optical measurement apparatus according to yet another embodiment of the invention employs fine grains having at least one wavelength among an exciting wavelength of the fluorescent substance and an emitting wavelength of the fluorescent substance, as the substance which absorbs light having at least one wavelength among an exciting wavelength of the fluorescent substance and an emitting wavelength of the fluorescent substance.

The apparatus includes a reaction vessel in which a reagent, including a fluorescent substance, and a test liquid for measurement are housed, so as to perform a predetermined reaction. The apparatus also has a casing which constituted the reaction vessel and a part which is constituted by an optical waveguide. The apparatus radiates an exciting light into the optical waveguide at a predetermined relative angle with respect to the optical waveguide. The apparatus then measures the optical characteristics in the vicinity of the surface of the optical waveguide within the reaction vessel, by receiving a fluorescent light component from fluorescent light due to the fluorescent substance. The fluorescent light component is output at a predetermined relative angle with respect to the optical waveguide. When the measurement is performed, the apparatus adds the fine-grains in the reaction vessel. The fine-grains absorb light which has at least one wavelength among an exciting wavelength of the fluorescent substance and an emitting wavelength of the fluorescent substance. The apparatus can thus prevent the fluorescent substance from being excited by scattering of the exciting light generated at the surface of the optical waveguide, which fluorescent substance is not constrained in the vicinity of the surface of the optical waveguide. Also the apparatus can prevent the fluorescent light which is radiated from the fluorescent substance from being introduced into the optical waveguide, which fluorescent substance is excited by the scattered exciting light which is generated at the surface of the optical waveguide. Therefore, the apparatus improves the S/N ratio of optical measurement.

An optical measurement apparatus according to an eighth embodiment of the invention employs water soluble dye which absorbs light having at least one wavelength among an exciting wavelength of the fluorescent substance and an emitting wavelength of the fluorescent substance.

This optical measurement apparatus includes a reaction vessel in which a reagent, including a fluorescent substance, and a test liquid for measurement are housed so as to perform a predetermined reaction. The apparatus also includes a casing which constitutes the reaction vessel and a part which is constituted by an optical waveguide. The apparatus radiates an exciting light into the optical waveguide at a predetermined relative angle with respect to the optical waveguide. The apparatus then measures the optical characteristics in the vicinity of the surface of the optical waveguide within the reaction vessel, by receiving a fluorescent light component from fluorescent light due to the fluorescent substance. The fluorescent light component is output of a predetermined relative angle with respect to the optical waveguide. When the measurement is performed, the apparatus adds a water soluble dye in the reaction vessel which absorbs light having at least one wavelength among an exciting wavelength of the fluorescent substance and an emitting wavelength of the fluorescent substance. The apparatus can thus prevent the fluorescent substance from being excited by scattering of the exciting light generated at the surface of the optical waveguide, which fluorescent substance is not constrained in the vicinity of the surface of the optical waveguide. Also the apparatus can prevent the fluorescent light radiated from the fluorescent substance from being introduced into the optical waveguide, which fluorescent substance is excited by the scattered exciting light generated at the surface of the optical waveguide. Therefore, the apparatus improves the S/N ratio of the optical measurement.

An optical measurement method according to a ninth embodiment of the invention is a method which performs a predetermined reaction within a reaction vessel between ligands which are made to be in solid phase on the surface of the optical waveguide, a test liquid for measurement which is pourd within the reaction vessel, and a reagent which includes ligands which are poured within the reaction vessel and which are labeled with a fluorescent substance. The method introduces an exciting light into the optical waveguide so as to propagate within the optical waveguide in a totally reflective manner. The method measures the optical characteristics in the vicnity of the surface of the optical waveguide based upon a fluorescent light component from fluorescent light radiated by the fluorescent substance. The fluoresecent light component propagates within the optical waveguide in a totally reflective manner. And, the method measures the optical characteristics in the vicinity of the surface of the optical waveguide by receiving the fluorescent light component under a condition where fine-grains are added in the reaction vessel to absorb light which has at least one wavelength among an exciting wavelength of the fluorescent substance and an emitting wavelength of the fluorescent substance.

That is, the method performs the predetermined reaction within the reaction vessel between ligands which are made to be in a solid phase on the surface of the optical waveguide, the test liquid for measurement which is poured within the reaction vessel, and the reagent which includes ligands which are poured within the reaction vessel and which are labeled with a fluorescent substance. The method introduces the exciting light into the optical waveguide to propagate within the optical waveguide in a totally reflective manner. The method then measures the optical characteristics in the vicinity of the surface of the optical waveguide based upon the fluorescent light component from the fluorescent light radiated by the fluorescent substance, which component propagates within the optical waveguide in a totally reflective manner. And, the method measures the optical characteristics in the vicinity of the surface of the optical waveguide by receiving the fluorescent light component under a condition where fine-grains are added in the reaction vessel to absorb light which has at least one wavelength among an exciting wavelength of the fluorescent substance and an emitting wavelength of the fluorescent substance. Therefore, the method can prevent the fluorescent substance from being excited by scattering of the exciting light generated at the surface of the optical waveguide, which fluorescent substance is not constrained in the vicinity of the surface of the optical waveguide. Also, the method can prevent the fluorescent light radiated from the fluorescent substance from being introduced into the optical waveguide, which fluorescent substance is excited by the scattered exciting light generated at the surface of the optical waveguide. Thus, the method improves the S/N ratio of the optical measurement.

An optical measurement method according to a tenth embodiment of the invention is a method which performs a predetermined reaction within a reaction vessel between ligands which are made to be in a solid phase on the surface of the optical waveguide, a test liquid for measurement which is poured within the reaction vessel, and a reagent which includes ligands which are poured within the reaction vessel and which are labeled with a fluorescent substance. The method introduces an exciting light into the optical waveguide so as to propagate within the optical waveguide in a totally reflective manner, and then measures the optical characteristics in the vicinity of the surface of the optical waveguide based upon a fluorescent light component from fluorescent light radiated by the fluorescent substance. The fluorescent light component also propagates within the optical waveguide in a totally reflective manner. The method measures the optical characteristics in the vicinity of the surface of the optical waveguide by receiving the fluorescent light component under a condition where a water soluble dye is added in the reaction vessel to absorb light which has at least one wavelength among an exciting wavelength of the fluorescent substance and an emitting wavelength of the fluorescent substance.

That is, this method performs the predetermined reaction within the reaction vessel between ligands which are made to be in a solid phase on the surface of the optical waveguide, the test liquid for measurement which is poured within the reaction vessel, and the reagent which includes ligands which are poured within the reaction vessel and which are labeled with a fluorescent substance. The method introduces the exciting light into the optical waveguide so as to propagate within the optical waveguide in a totally reflective manner. The method then measures the optical characteristics in the vicinity of the surface of the optical waveguide based upon the fluorescent light component from the fluorescent light radiated by the fluorescent substance. The fluorescent light component propagates within the optical waveguide in a totally reflective manner. And, the method measures the optical characteristics in the vicinity of the surface of the optical waveguide by receiving the fluorescent light component under a condition where a water soluble dye are added in the reaction vessel to absorb light which has at least one wavelength among an exciting wavelength of the fluorescent substance and an emitting wavelength of the fluorescent substance. Therefore, the method can prevent the fluorescent substance from being excited by scattering of the exciting light generated at the surface of the optical waveguide, which fluorescent substance is not constrained in the vicinity of the surface of the optical waveguide. Also the method can prevent the fluorescent light radiated from the fluorescent substance from being introduced into the optical waveguide, which fluorescent substance is excited by the scattered exciting light generated at the surface of the optical waveguide. Further, the method improves the S/N ratio of the optical measurement.

An optical measurement method according to another embodiment of the invention is a method which performs a predetermined reaction within a reaction vessel between ligands which are made to be in a solid phase on the surface of the optical waveguide, a test liquid for measurement which is poured within the reaction vessel, and a reagent which includes ligands which are poured within the reaction vessel and which are lebeled with fluorescent substance. The method introduces an exciting light into the optical waveguide at a predetermined relative angle with respect to the optical waveguide. The method then measures the optical characteristics in the vicinity of the surface of the optical waveguide based upon a fluorescent light component from fluorescent light radiated by the fluorescent substance. The fluorescent light component is output from the optical waveguide at a predetermined relative angle with respect to the optical waveguide. And, the method measures the optical characteristics in the vicinity of the surface of the optical waveguide by receiving the fluorescent light component under a condition where a substance is added in the reaction vessel which absorbs light having at least one wavelength among an exciting wavelength of the fluorescent substance and an emitting wavelength of the fluorescent substance.

That is, the method performs the predetermined reaction within the reaction vessel between ligands which are made to be in a solid phase on the surface of the optical waveguide, the test liquid for measurement which is poured within the reaction vessel, and the reagent which includes ligands which are poured within the reaction vessel and which are labeled with fluorescent substance. The method introduces the exciting light into the optical waveguide at a predetermined relative angle with respect to the optical waveguide. The method then measures the optical characteristics in the vicinity of the surface of the optical waveguide based upon the fluorescent light component from the fluorescent light radiated by the fluorescent substance. The fluorescent light component is output from the optical waveguide at a predetermined relative angle with respect to the optical waveguide. And, the method measures the optical characteristics in the vicinity of the surface of the optical waveguide by receiving the fluorescent light component under a condition where a substance is added in the reaction vessel to absorb light which has at least one wavelength among an exciting wavelength of the fluorescent substance and an emitting wavelength of the fluorescent substance. Therefore, the method can prevent the fluorescent substance from being excited by scattering of the exciting light generated at the surface of the optical waveguide, which fluorescent substance is not constrained in the vicinity of the surface of the optical waveguide. Also, the method can prevent the fluorescent light radiated from the fluorescent substance from being introduced into the optical waveguide, which fluorescent substance is excited by the scattered exciting light generated at the surface of the optical waveguide. The method thus improves an S/N ratio of optical measurement.

An optical measurement method according to yet another embodiment of the invention employs a method as the optical measurement method according to claim 11, which method radiates the exciting light so as to introduce the exciting light into the reaction vessel through the optical waveguide. The method measures optical characteristics in the vicinity of the surface of the optical waveguide based upon a fluorescent light component from the fluorescent light radiated by the fluorescent substance, which component propagates within the optical waveguide in a reflection manner.

That is, the method can prevent the fluorescent substance from being excited by scattering of the exciting light generated at the surface of the optical waveguide, which fluorescent substance is not constrained in the vicinity of the surface of the optical waveguide. Also, the method can prevent the fluorescent light which is radiated from the fluorescent substance from being introduced into the optical waveguide, which fluorescent substance is excited by the scattered exciting light generated at the surface of the optical waveguide. The method thus improves the S/N ratio of optical measurement, because the method employs the method as the optical measurement method according to the previous embodiment of the invention which method radiates the exciting light so as to introduce the exciting light into the reaction vessel through the optical waveguide. The method measures the optical characteristics in the vicinity of the surface of the optical waveguide based upon a fluorescent light component from the fluorescent light radiated from the fluorescent substance, which component propagates within the optical waveguide in a reflection manner.

An optical measurement method according to a thirteenth embodiment of the invention employs a method which radiates the exciting light so as to introduce the exciting light into the reaction vessel through the optical waveguide which exciting light propagates within the optical waveguide in a totally reflective manner. The method measures optical characteristics in the vicinity of the surface of the optical waveguide based upon a fluorescent light component from the fluorescent light radiated by the fluorescent substance, which component is output outward through the optical waveguide.

This method can prevent the fluorescent substance from being excited by scattering of the exciting light generated at the surface of the optical waveguide, which fluorescent substance is not constrained in the vicinity of the surface of the optical waveguide. Also, the method can prevents the fluorescent light which is radiated from the fluorescent substance from being output outward through the optical waveguide. The method improves the S/N ratio of the optical measurement, because the method radiates the exciting light so as to introduce the exciting light into the reaction vessel through the optical waveguide. The method measures the optical characteristics in the vicinity of the surface of the optical waveguide based upon a fluorescent light component from the fluorescent light which is radiated by the fluorescent substance, which component is output outward through the optical waveguide.

An optical measurement method according to another embodiment of the invention employs a method which radiates the exciting light so as to introduce the exciting light into the reaction vessel through the optical waveguide at a predetermined angle. The method measures optical characteristics in the vicinity of the surface of the optical waveguide based upon a fluorescent light component from the fluorescent light radiated from the fluorescent substance. The fluorescent light component is output outward through the optical waveguide at a predetermined angle which is different from that of the exciting light.

This method can prevent the fluorescent substance from being excited by scattering of the exciting light which is generated at the surface of the optical waveguide, which fluorescent substance is not constrained in the vicinity of the surface of the optical waveguide. Also, this method can prevent the fluorescent light which is radiated from the fluorescent substance from being output through the optical waveguide, which fluorescent substance is excited by the scattered exciting light generated at the surface of the optical waveguide. The method thus improves the S/N ratio of the optical measurement, because the method radiates the exciting light so as to introduce the exciting light into the reaction vessel through the optical waveguide at a predetermined angle. The method measures the optical characteristics in the vicinity of the surface of the optical waveguide based upon a fluorescent light component from the fluorescent light radiated by the fluorescent substance, which component is output outward through the optical waveguide at a predetermined angle which is different from that of the exciting light.

An optical measurement method according to yet another embodiment of the invention employs fine-grains which absorb light having at least one wavelength among an exciting wavelength of the fluorescent substance and an emitting wavelength of the fluorescent substance.

The method can thus prevent the fluorescent substance from being excited by scattering of the exciting light generated at the surface of the optical waveguide, which fluorescent substance is not constrained in the vicinity of the surface of the optical waveguide. Also, the method can prevent the fluorescent light which is radiated from the fluorescent substance from being introduced into the optical waveguide, which fluorescent substance is excited by the scattered exciting light generated at the surface of the optical waveguide. The method thus improves the S/N ratio of the optical measurement, because the method employs fine-grains which absorb light at of least one wavelength among the exciting wavelengths of the fluorescent substance and an emitting wavelength of the fluorescent substance.

An optical measurement method according to a sixteenth embodiment of the invention employs a water soluble dye which absorbs light having at least one wavelength among an exciting wavelength of the fluorescent substance and an emitting wavelength of the fluorescent substance.

This method can prevent the fluorescent substance from being excited by scattering of the exciting light generated at the surface of the optical waveguide, which fluorescent substance is not constrained in the vicinity of the surface of the optical waveguide. Also, this method can prevent the fluorescent light which is radiated from the fluorescent substance from being introduced into the optical waveguide, which fluorescent substance is excited by the scattered exciting light generated at the surface of the optical waveguide. The method thus improves the S/N ratio of optical measurement, because the method employs a water soluble dye which absorbs light of at least one wavelength among the exciting wavelength of the fluorescent substance and an emitting wavelength of the fluorescent substance.

BEST MODE FOR IMPLEMENTING THE INVENTION

Hereinafter, referring to the attached drawings, the present invention is explained in detail.

Figure 1:
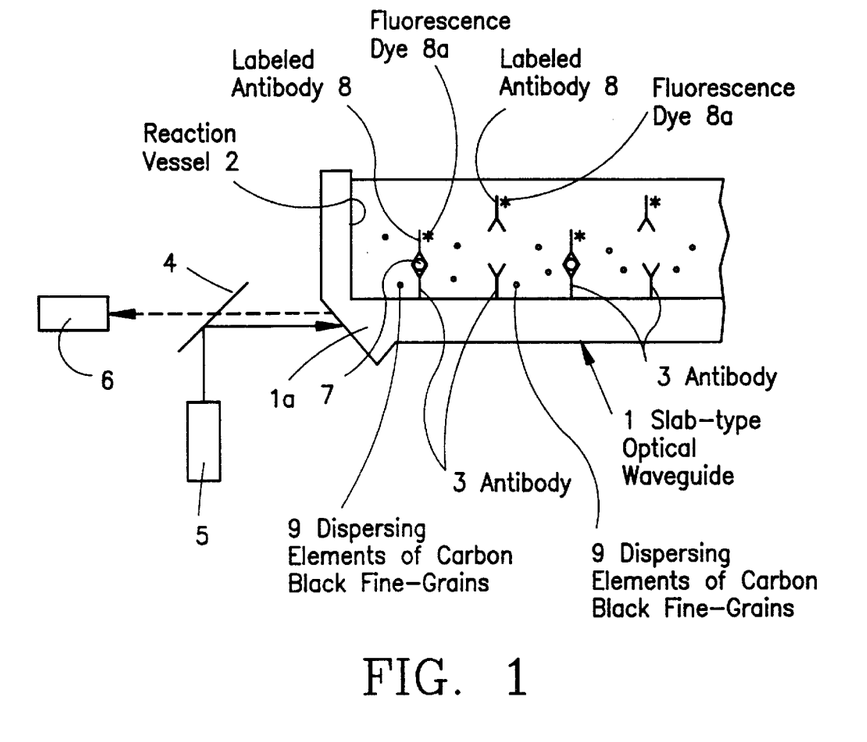
FIG. 1 is a schematic vertical cross sectional view illustrating an embodiment of an optical measurement apparatus according to the present invention.

FIG. 1 is a schematic vertical cross sectional view illustrating an embodiment of an optical measurement apparatus acording to the present invention. A prism 1a for introducing an exciting light is formed unitary body at one end of a slab-type optical waveguide 1. A reaction vessel 2 is formed unitary body on one side of the slab-type optical waveguide 1. A plurality of antibodies 3 are fixed on one side of the slab-type optical waveguide 1. A dichroic mirror 4, an exciting light source 5 and a light receiving element 6 such as a photomultiplier or the like are disposed at a predetermined relative position with respect to the slab-type optical waveguide 1. The dichroic mirror 4 separates a light path of the exciting light which is introduced into the slab-type optical waveguide 1 through the prism 1a, and a light path of a fluorescent light which is output through the prism 1a.

When an immunity measurement using fluorescent light is carried out with using the optical measurement apparatus having the above arrangement, a test liquid for measurement is housed in the reaction vessel 2 so that an antigen-antobody reaction is obtained between antigens 7 in the test liquid for measurement and the fixed antibodies 3 under a condition that the exciting light source 5 is operated. Then, the test liquid for measurement is discharged from the reaction vessel 2. Next, a reagent liquid which includes labeled antibodies 8 made by labeling antibodies with fluorescent dye 8a and to which are added dispersing elements 9 {0.04%(w/v)} of fine grains of carbon black having a grain diameter of about 200 nm, is housed in the reaction vessel 2. An antigen-antibody reaction is carried out between the antigens 7 which have already undergone an antigen-antibody reaction, and the labeled antibodies 8. Therefore, the labeled antibodies 8 are constrained in the vicinity of the slab-type optical waveguide 1 in a quantity which corresponds to a concentration of the antigens 7 in the test liquid for measurement.

When the process is carried out, an evanescent wave component due to the exciting light is generated. The exciting light is scattered at the surface of the slab-type optical waveguide 1, but, a scattered component of the exciting light, and the fluorescent light radiated from fluorescent dye of the labeled antibodies 8 which are not constrained in the vicinity of the surface of the slab-type optical waveguide 1 (hereinafter, referred to as stray light), are effectively absorbed so that the S/N ratio of the optical immunity measurement is improved. This is due to the dispersing elements 9 of fine grains of carbon black added in the reagent liquid.

Figure 2:
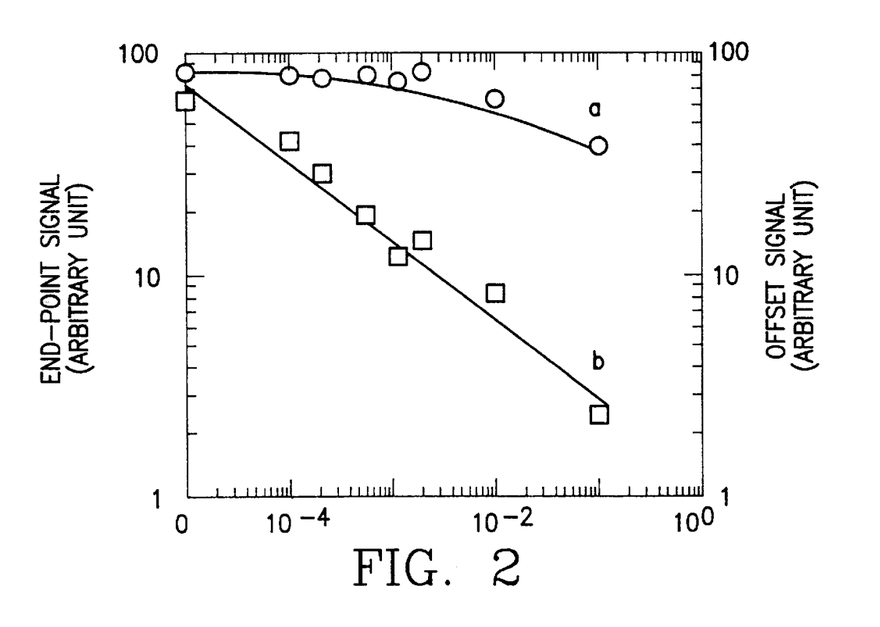
FIG. 2 is a graph illustrating the variation of an end-point signal and an offset signal with respect to a concentration of dispersing elements of fine grains of carbon black.

FIG. 2 is a graph illustrating the variation of an end-point signal and an offset signal with respect to a concentration of dispersing elements of fine grains of carbon black. In FIG. 2, a represents the end-point signal, while b represents the offset signal. Further, a concentration of carbon black is indicated with a magnification in dilution (dilution magnification) with respect to an absorber which includes fine grains of carbon black of 31.5 w/v). As is apparent from FIG. 2, the decrease in the end-point signal is gentle, while the decrease in the offset signal is steep. That is, the S/N ratio of the immunity measurement using the fluorescent light is improved by a simple processing i.e., the adding of the dispersing elements of fine grains of carbon black. When an amount of decrease of the end-point signal is less than 10% and in which the amount of the offset signal is lowering, is determined to be an effective extent, the dilution magnification of the absorber which includes fine grains of the variation, is $10^{-4}$–$10^{-2}$. When the dilution magnification is converted to a concentration of fine grains of carbon black, the concentration is about 0.004–0.3%.

Figure 3:
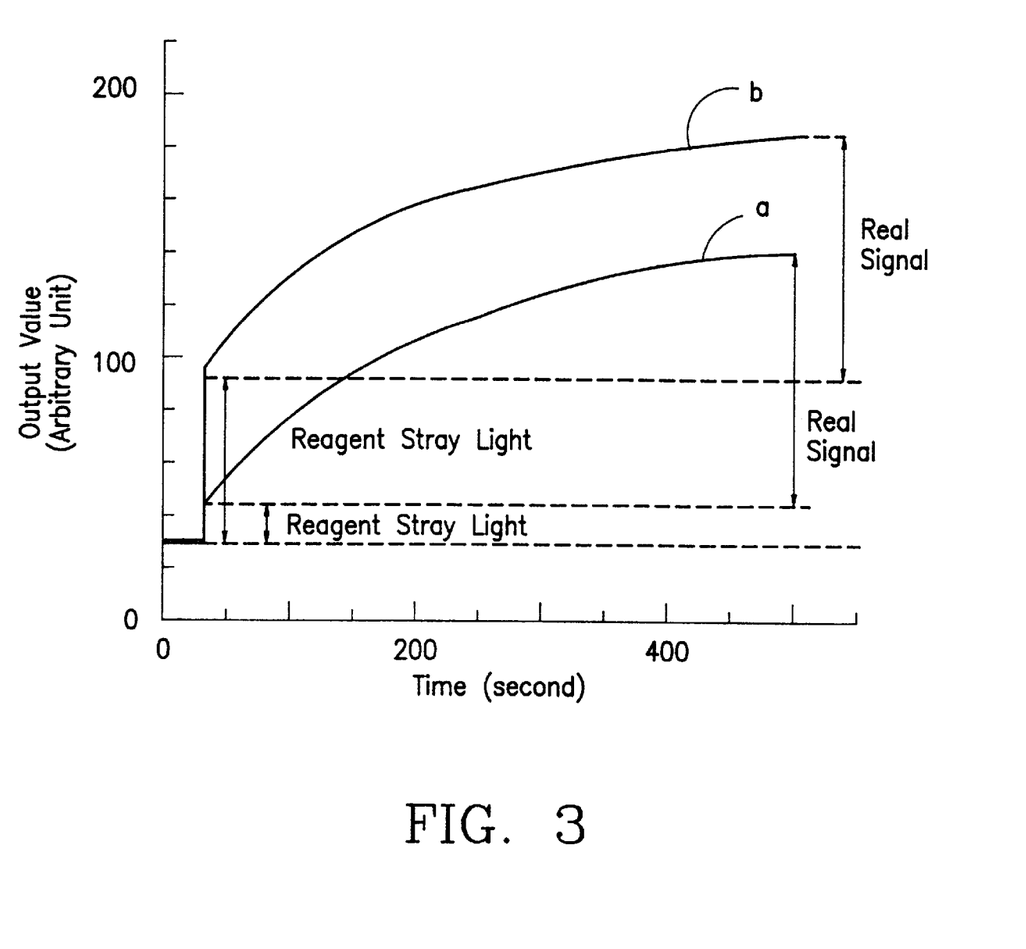
FIG. 3 is a graph illustrating the variation of an immunity measurement signal using fluorescent light following the passage of time.

Further, a variation of an immunity measurement signal using fluorescent light following the passage of time, under a condition where dispersing elements of fine grains of carbon black are added, and a variation of an immunity measurement signal using fluorescent light following the passage of time under a condition that dispersing elements of carbon black are not added, are illustrated in FIG. 3. In FIG. 3, In FIG. 3, a represents the former case, while b represents the latter case.

As is apparent from FIG. 3, when grains of carbon black are not added, the signal is increased and the reagent stray light is also increased as is illustrated by b. On the constrary, when fine grains of carbon black are added, the signal is decreased to some degree and the reagent stray light is remarkably decreased as is illustrated by a. Therefore, the S/N ratio is remarkably improved.

Further, it is possible to employ that fine grains of metal such as platinum, gold or the like, or fine grains of polyethylene instead of the fine grains of carbon black. In this case, effects which are similar to the above effects are achieved.

Second Embodiment

An immunity measurement using fluorescent light was carried out with the optical measurement apparatus illustrated in FIG. 1, using a He—Ne laser excitation wavelength of 633 nm as the exciting light source 5, and using a reagent liquid made by adding the labeled antibodies and cyanogen 1P (manufactured by Nihon Kayahu Kabushiki Gaisha). Also, immunity measurements using fluorescent light were carried out using a reagent liquid made by adding only the antibodies, and using a reagent liquid which is made by adding Blue 50p (manufactured by Nihon Kayahu Kabushiki Gaisha) instead of cyanogen 1P, respectively.

Figure 4:
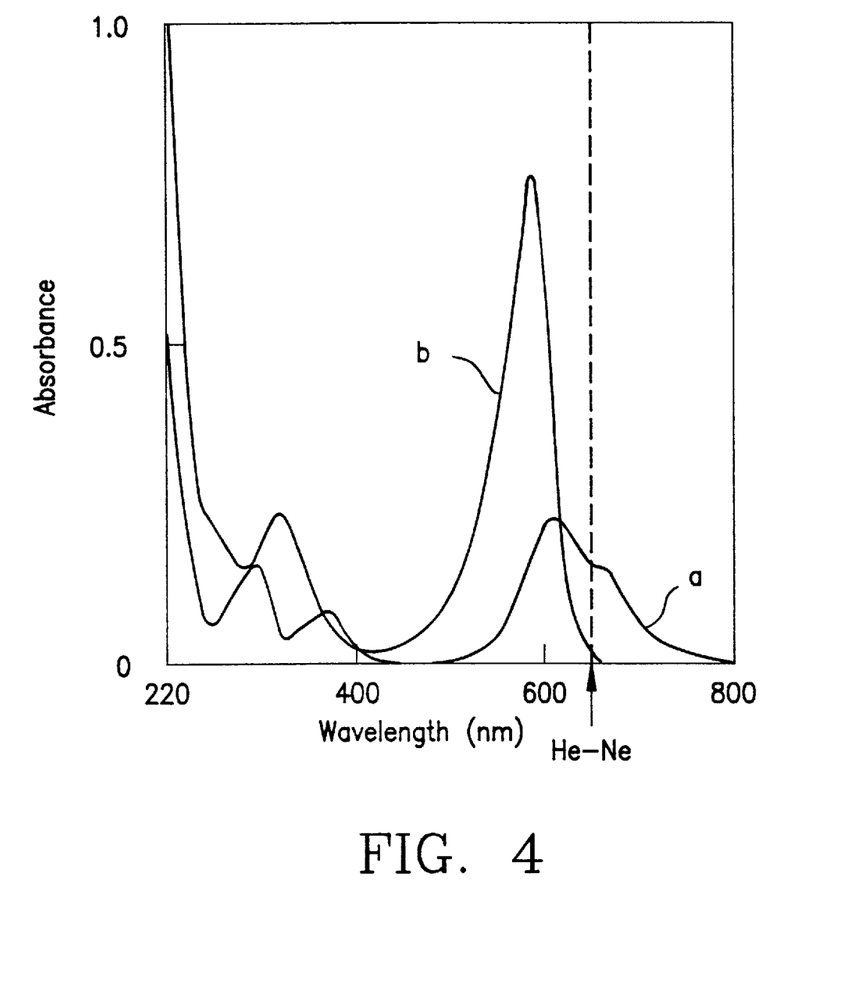
FIG. 4 is a graph illustrating the wavelength dependency to the absorbance of cyanogen 1P and Blue 50p.

As a result, when the cyanogen 1P was added, the reagent stray light was 36.0 (arbitrary units) so that a lessening effect in the reagent stray light was achieved. This is compared to a reagent stray light of 61.1 when the reagent liquid with only the antibodies was used. When Blue 50p is added (which does not absorbs the exciting wavelength of 633 nm), the reagent stray light was 497 as is illustrated by b in FIG. 4. The reason for this remarkable increase in the reagent stray light seems to be that Blue 50p conduced scattering of the exciting light. Further, a in FIG. 4 illustrates an absorbance characteristic of cyanogen 1P. It is understood that cyanogen 1P has a fairly high absorbance of light with a wavelength of 633 nm.

Figure 5:
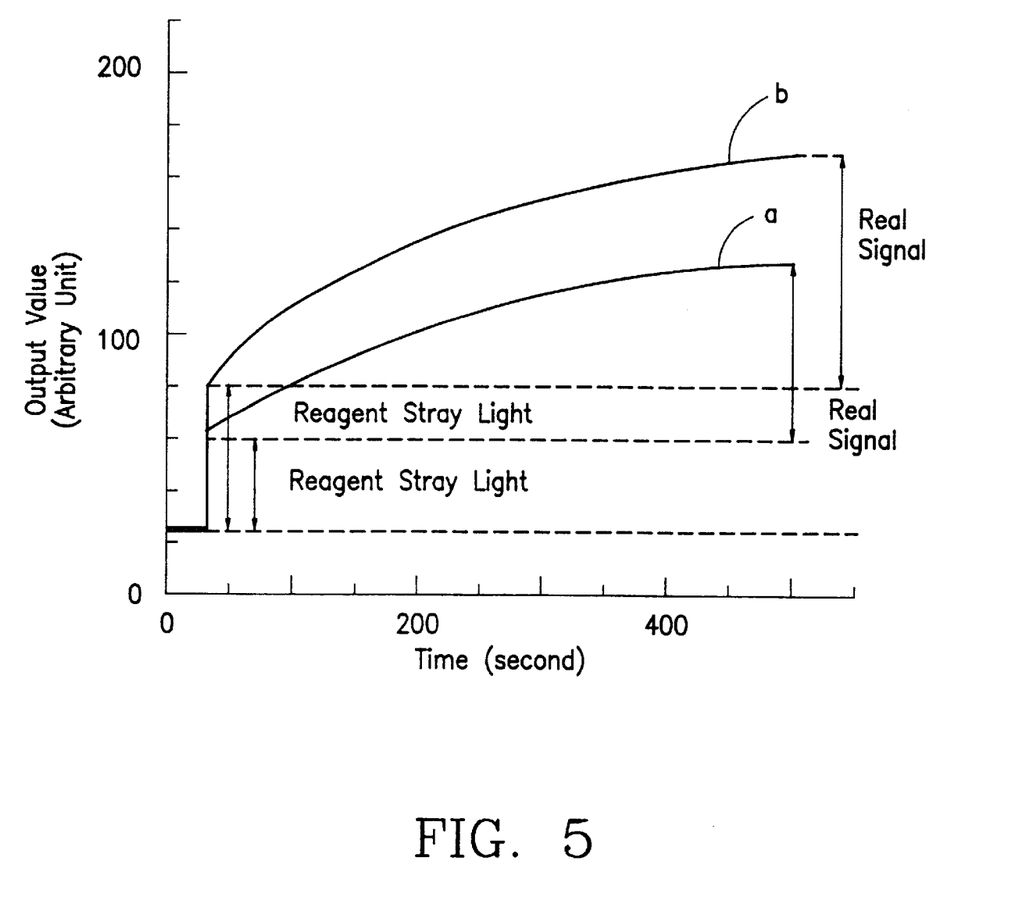
FIG. 5 is a graph illustrating the variation of an immunity measurement signal using fluorescent light following the passage of time.

Further, a variation of immunity measurement signals using fluorescent light following the passage of time under a condition where only labeled antibodies were added, and a variation of immunity measurement signals using fluorescent light following the passage of time under a condition where cyanogen 1P and labeled antibodies were added, are illustrated in FIG. 5.

As is apparent from FIG. 5, when only the labeled antibodies were added, not only was the signal increased, but the reagent stray light also is increased, as is illustrated by b in FIG. 5. Comparatively, when cyanogen 1P and the labeled antibodies were added, the signal was lessened to some degree and the reagent stray light was remarkably lessened as is illustrated by a in FIG. 5. Therefore, the S/N ratio was reamrkably improved.

The foregoing describes a case where a water soluble dye is used which has a high absorbance for the wavelength of the exciting light. It also is possible to use a water soluble dye which has a high absorbance for the wavelength of fluorescent light which is radiated from the fluorescent dye. It is also possible to use a water soluble dye which has a high absorbance for both the wavelength of the exciting light and for the wavelength of fluorescent light which is radiated from the fluorescent dye. Further, various design change within an extend which does not vary the scope of the present invention, are possible.

Third Embodiment

FIG. 5 is a schematic vertical cross sectional view illustrating another embodiment of an optical measurement apparatus according to the present invention. A prism 1a for introducing an exciting light is formed at one end of a slab-type optical waveguide 11. A reaction vessel 12 is formed unitary body on one side of the slab-type optical waveguide 11. A plurality of antibodies 13 are fixed on one side of the slab-type optical waveguide 11. A signal light output through the prism 11a is guided to a light receiving element 16 such as a photomultiplier, through a sharp cut filter or the like (not illustrated). An light output from an exciting light source 15, such as a laser light source or the like, is radiated as a plane wave to the other side of the slab-type optical waveguide 11 through a collimator lens 14a, neutral density filter (hereinafter, referred to as a ND filter) 14b and the like. The temperature of the exiting light source 15 is controlled by a temperature controlling section (not illustrated) so that a variation in the intensity of the output light is prevented from occuring. The slab-type optical waveguide 11 and the reaction vessel 12 have their faces painted (faces which are parallel to the paper in FIG. 6, and hereinafter, referred to simply as side faces,) with black paint or the like. The side faces do not cross an optical axis of the exciting light (or an axis which is parallel to the optical axis of the exciting light) and do not cross an optical axis of the signal light (or an axis which is parallel to the optical axis of the signal light). Therefore, light is prevented from being output from the side faces. When it is assumed that light is output, there is a possibility that the output light is received by the light receiving element 16 through various paths. However, such light is prevented by the paint from being received by the light receiving element 16. Of course, light also is prevented from being incident from the exterior through the side faces.

Figure 6:
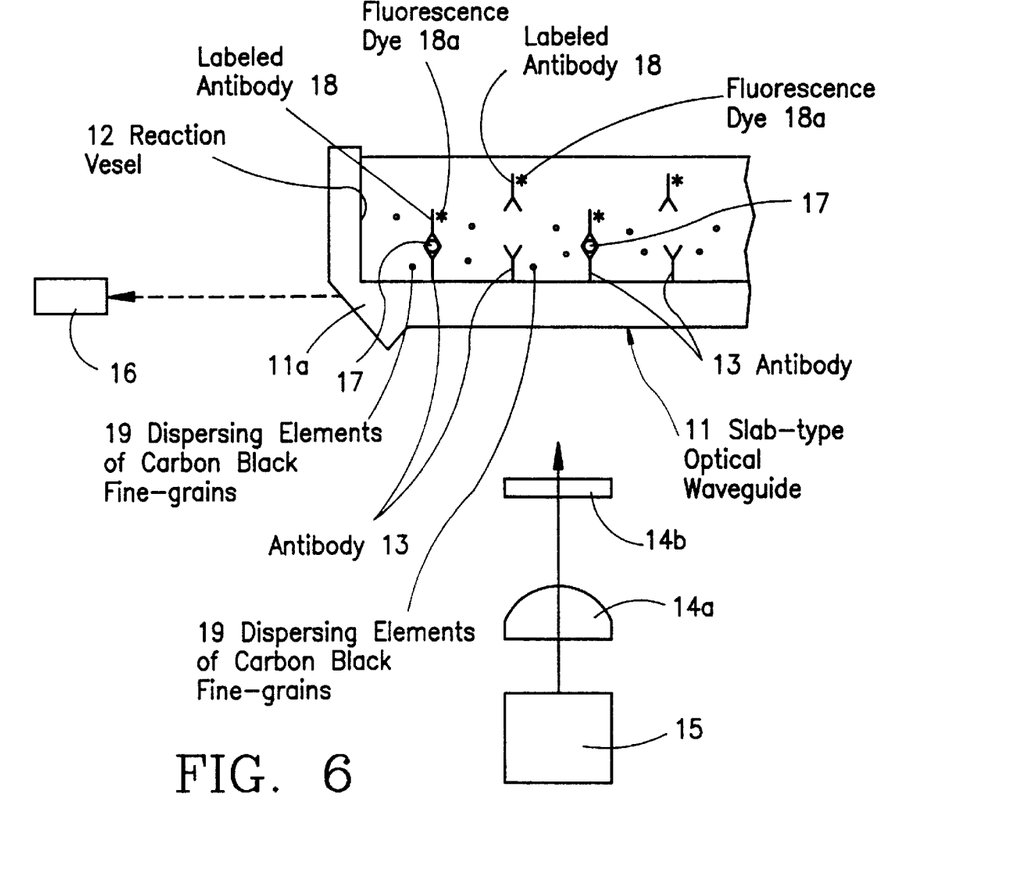
FIG. 6 is a schematic vertical cross sectional view illustrating another embodiment of an optical measurement apparatus according to the present invention.

When an immunity measurement using fluorescent light is carried out using the optical measurement apparatus having the above arrangement, a test liquid for measurement is housed in the reaction vessel 12 so that the antigen-antibody reaction between antigens 17 in the test liquid for measurement and the fixed antibodies 13 are under a condition where the exciting light source 15 is operated. Then, the test liquid for measurement is discharged from the reaction vessel 12. Then, a reagent liquid which includes labeled antibodies 18, made by labeling antibodies with fluorescent dye 18a, added with fine grains of carbon black 19 (in a desired concentration) having a desired grain diameter, is housed in the reaction vessel 12 so that an antigen-antibody reaction is carried out between the antigens 17 which have already undergone the antigen-antibody reaction, and the labeled antibodies 18. Therefore, the labeled antibodies 18 are constrained in the vicinity of the slab-type optical waveguide 11 in a quantity which corresponds to a concentration of the antigens 17 in the test liquid for measurement.

When the process is carried out, the plane wave of exciting light is introduced into the reaction vessel 12 through the slab-type optical waveguide 11 in a direction of the thickness thereof. Because the reagent liquid has fine grains of carbon black 19, the plane wave is absorbed within the reaction vessel 12 efficiently in its early stage so that a disadvantage is remarkably reduced wherein fluorescent dye 1a is labeled antibodies 18 are excited which are apart from the surface of the slab-type optical waveguide 11. When it is assumed that the fluorescent dye 1a of labeled antibodies 18 radiate fluorescent light, which antibodies are apart from the surface of the slab-type optical waveguide 11, the radiated fluorescent light is effectively absorbed so that the possibility of mixing the radiated fluorescent light with the signal light is remarkably reduced, which signal light propagates within the slab-type optical waveguide 11. Therefore, the sensitivity of the optical immunity measurement (S/N ratio) is remarkably improved.

In the optical measurement apparatus having the above arrangement, a mixture of undiluted milk protein and sodium azide (NaN3;0.02%) was coated as a blocking member instead of fixing a plurality of antibodies 13 on the side of the slab-type optical waveguide 11. And, a reagent {CMI (Carboxymethylindocyanine)-IgG (Immunoblobulin-G), 4 $\mu$g/ml} in which fine grains of carbon black 19 (diluted by a dilution liquid so as to be 1 weight %), and a reagent (CMI-IgG, 4 $\mu$g/ml) in which fine grains of carbon black 19 were not added, were poured by 400 $\mu$l, respectively. The intensities of the output light prior to and after the pouring were measured. Further, a slab-type optical waveguide 11 was employed which was painted with black paint for screening stray light on its surfaces adjacent to the signal light outgoing surface. And, a reagent {CMI-IgG, 4 $\mu$g/ml} in which fine grains of carbon black 19 (diluted by a dilution liquid so as to be 1 weight %), and a reagent (CMI-IgG, 4 $\mu$g/ml) in which no carbon black 19 was added, were poured by 400 $\mu$l, respectively, and the intensities of the output light prior to and after the pouring were measured. For this measurement, a laser light source was employed as the exciting light source 15. Here the exciting light was cut by 10% by the ND filter, and the plane wave of 3×10 mm was radiated from below the slab-type optical waveguide 11.

As a result of the above measurement, when the reagent in which fine grains of carbon black 19 were not added was used, and the slab-type optical waveguide 11 was not painted with black paint the signal values (the signal value is an output pulse number of the photomultiplier, and corresponds to the intensity of output light) prior to and after the pouring were 0.2397 kilo pulse per second (hereinafter, referred to as kpps) and 140.2016 kpps respectively. When the reagent in which fine grains of carbon black 19 were not added, was used, and the slab-type optical waveguide 11 was painted with black paint for screening stray light, the signal values prior to and after the pouring were 0.2234 kpps and 42.4969 kpps respectively. When the reagent in which carbon black 19 were added, was used, and the slab-type optical waveguide 11 was not painted, the signal values prior to and after the pouring were 0.2717 kpps and 0.2563 kpps respectively. When the reagent in which fine grains of carbon black 19 were added, was used, and the slab-type optical waveguide 11 was painted with black paint for screening stray light, the signal values prior to and after the pouring were 0.2048 kpps and 0.2076 kpps respectively.

In those measurement, milk protein (mixed sodium azide by 0.02%) as a blocking member was coated on the surface of the slab-type optical waveguide 11. Therefore no reagent existed in the vicinity of the surface of the slab-type optical waveguide 11. The output light prior to pouring of the reagent is an offset value due to fluorescent light which is generated in the slab-type optical waveguide 11 itself, and nearly the same signal values were obtained for each case. But, after the pouring of the reagent, the greatest signal value is obtained when neither fine grains of carbon black 19 nor black paint for screening stray light were applied. The second greatest signal value was obtained when only black pint for screening stray light was applied. A signal value which is nearly the same to the signal value at prior to pouring, was obtained when fine grains of carbon black 19 were applied. As is apparent from the result, reagent stray light was detected to some degree in the former two cases. On the contrary, reagent stray light was sufficiently reduced in the latter two cases. Further, the signal value after the pouring of the reagent was slightly smaller than that prior to the pouring of the reagent, due to the influence of variation in the refractive index from the pouring of the reagent.

Further, when the slab-type optical waveguide (where black paint for screening stray light was not painted) having the arrangement which was the same as the above arrangement, other than the coating of milk protein (mixed sodium azide by 0.2%) is omitted, and colored reagent ink was poured in the reaction vessel by 200 µl which ink a concentration of 1 weight %, the signal values prior to and after the pouring were 0.080 kpps and 1.600 kpps, respectively. In this case, milk protein (mixed sodium azide by 0.2%) as blocking member was not coated on the surface of the slab-type optical waveguide 11 so that the reagent exised in an exciting region which corresponds to the vicinity of the surface of the slab-type optical waveguide 11. Therefore, it is guessed that the signal component due to the actual immunity reaction was sufficiently taken out. Further, the signal values prior to the pouring for the above four cases where milk protein (mixed sodium azide by 0.02%) was coated on the surface of the slab-type optical waveguide 11 as a blocking member, were greater than the signal value prior to pouring of the colored reagent ink in the above measurement. The reason seems to be that milk protein (mixed sodium azide by 0.02%) as a blocking member was coated on the surface of the slab-type optical waveguide 11.

Figure 7:
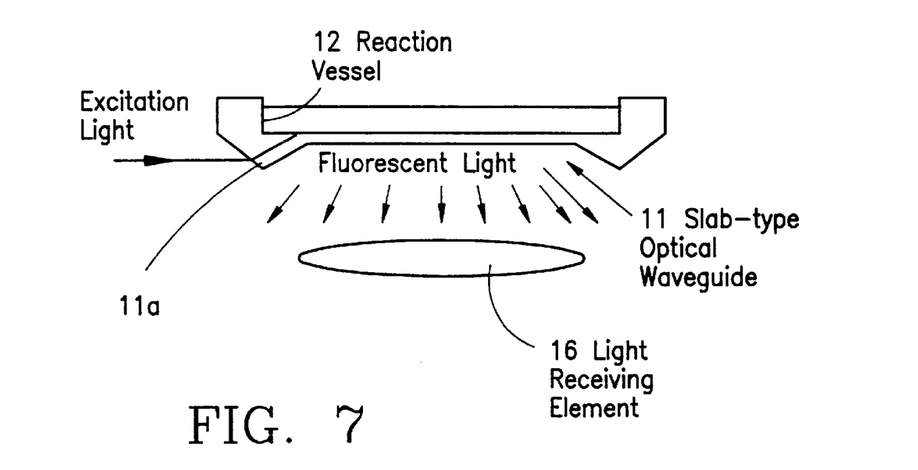
FIG. 7 is a schematic vertical cross sectional view illustrating a further embodiment of an optical measurement apparatus acording to the present invention.

In this embodiment, the exciting light is introduced into the reaction vessel 12 from below the slab-type optical waveguide 11, the signal light is propagated within the slab-type optical waveguide 11 so that the signal light is output through the prism 11a. It is possible to introduce the exciting light through the prism 11a so that the exciting light propagates within the slab-type optical waveguide 11, and the signal light is output from the bottom face of the slab-type optical waveguide 11, and received by the light receiving element 16, as is illustrated in FIG. 7. It is also possible that the exciting light is radiated at a predetermined angle with respect to the bottom face of the slab-type optical waveguide 11, and the signal light which is output from the bottom face of the slab-type optical waveguide 11 at an angle which is different from that of the exciting light, is received by the light receiving element, as is illustrated in FIG. 8.

Figure 8:
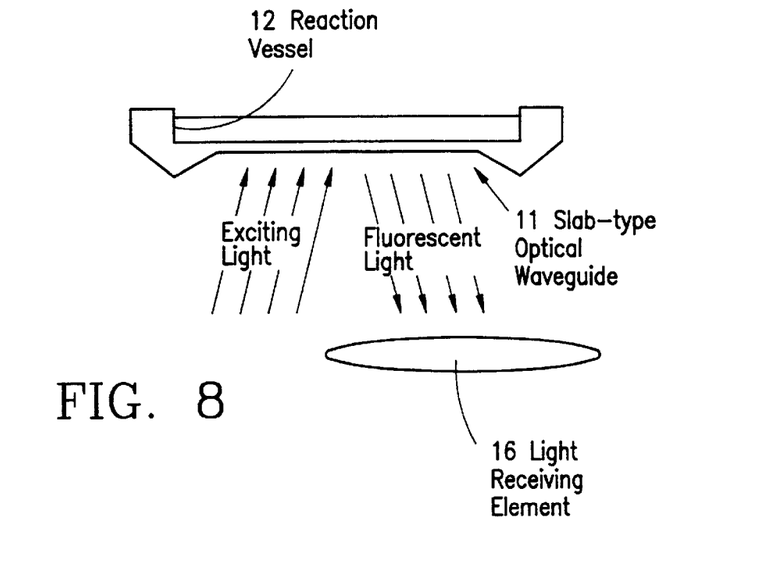
FIG. 8 is a schematic vertical cross sectional view illustrating yet another embodiment of an optical measurement apparatus according to the present invention.

Further, in the optical measurement apparatus illustrated in FIGS. 6–8, it is possible that fine grains of metal such as platinum, gold or the like, or fine grains of polystyrene and or the like are employed instead of carbon black. It is also possible that a water soluble dye having a high absorbance for the wavelength of the exciting light, a water soluble dye having a high absorbance for the fluorescent light which is radiated from the fluorescent dye, or a water soluble dye having a high absorbance for both lights, is employed instead of carbon black.

Fourth Embodiment

Figure 9:
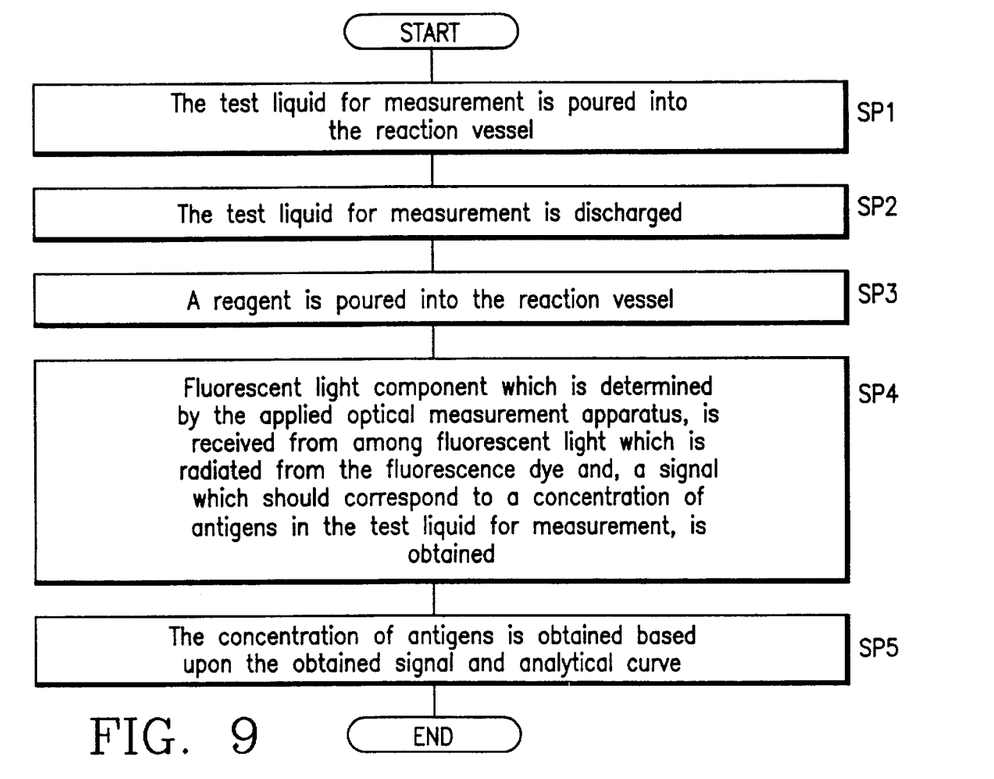
FIG. 9 is a flow chart which explains an embodiment of an optical measurement method according to an embodiment of the present invention.

FIG. 9 is a flowchart which explains an embodiment of an optical measurement method according to the present invention. The flowchart represents a case in which an optical measurement is carried out using the optical measurement apparatus described in one of the above embodiments. Therefore, antibodies 3, 13, for example, are previously fixed on the surface of the slab-type optical waveguide 1, 11, which surface constitutes one face of the reaction vessel 2, 12.

When starting of an immunity measurement is instructed, in step SP1, the test liquid for measurement is poured into the reaction vessel 2, 12 using a pouring nozzle 32a (refer to FIG. 10) so that an antigen-antibody reaction is carried out between the previously fixed antibodies 3, 13 and the antigens 7, 17 in the test liquid for measurement. After the antigen-antibody reaction is carried out for a predetermined time, in step SP2, the test liquid for measurement is discharged from the reaction vessel 2, 12 using the pouring nozzle 32a. In step SP3, a reagent which includes an absorbant substance (a substance which absorbs light having at least one wavelength among the exciting wavelength for exciting the fluorescent dye, and the emitting wavelength of the fluorescent dye) in a desired concentration, is poured into the reaction vessel 2, 12 using the pouring nozzle 32a. An antigen-antibody reaction then is carried out between antigens 7, 17 which are constrained in the vicinity of the surface of the slab-type optical waveguide 1, 11 by the antigen-antibody reaction which has already been carried out, and labeled antibodies 8, 18 in the reagent. In step SP4, a fluorescent light component which is determined by the applied optical measurement apparatus, is received by the light receiving element 6, 16 from the fluorescent light radiated by the fluorescent dye 8a, 18a of the labeled antibodies 8, 18 constrained in the vicinity of the surface of the slab-type optical waveguide by the antigen-antibody reaction. A signal which should correspond to a concentration of antigens 7, 17 in the test liquid for measurement, is thus obtained. In step SP5, the concentration of antigens 7, 17 in the test liquid for measurement is obtained based upon the obtained signal and a previously obtained analytical curve. Then, the process is finished.

The processing in step SP3 and the processing in step SP4 are carried out simultaneously to one another. it is preferable that the processing in step SP4 is started prior to the processing in step SP3. In this case, an offset noise due to the slab-type optical waveguide 1, 11 is obtained by following data processing (not illustrated). The signal obtained in step SP4 may be obtained by waiting until a signal value becomes nearly saturated, which signal value is varied following the advancing in the antigen-antibody reaction, and by obtaining the signal value at the nearly saturated timing. The signal may also be obtained by continuously calculating a differential value by time of a signal which is varied following the advancing in the antigen-antibody reaction, and by employing the maximum value of the differential value by time.

Figure 10:
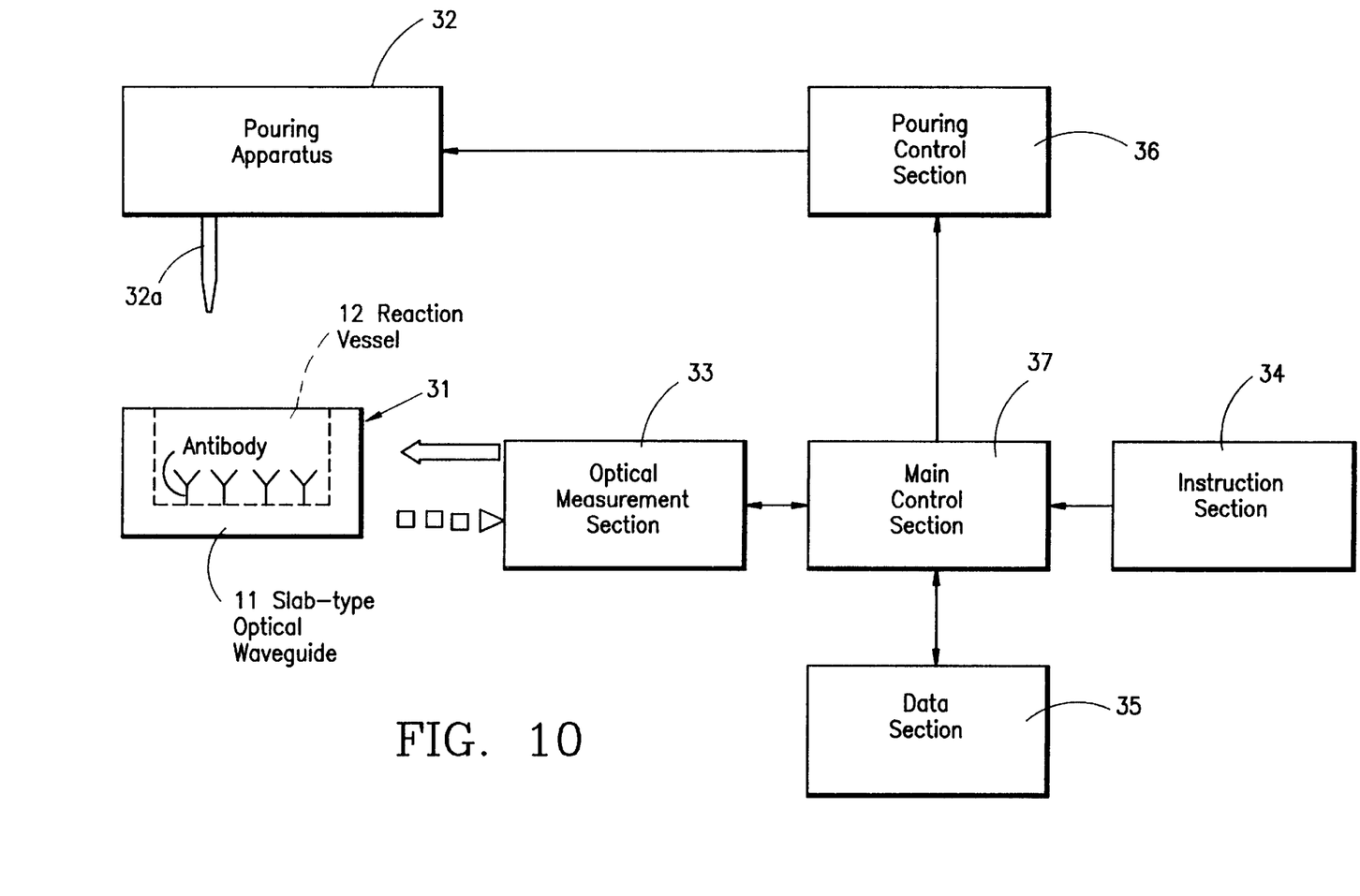
FIG. 10 is a block diagram illustrating a schematic arrangement of an optical measurement apparatus to which the flowchart illustrated in FIG. 9 is applied.

FIG. 10 is a block diagram illustrating a schematic arrangement of an optical measurement apparatus to which the flowchart illustrated in FIG. 9 is applied. The apparatus includes a measurement cell 31 which has a reagent housing vessel (not illustrated), a test liquid housing vessel (not illustrated), and a dilution liquid housing vessel (not illustrated), and a reaction vessel 12 for carrying out the antigen-antibody reaction. Also a slab-type optical waveguide 11 is formed in a predetermined face of the reaction vessel 12, on which the antibodies 13 are fixed. The apparatus further includes a pouring apparatus 32, an optical measurement section 33, an instruction section 34, a data section 35, a pouring control section 36 and a main control section 37. The pouring apparatus 32 has a pouring nozzle 32a for pouring liquid into any of the vessels, and for sucking and removing liquid from any of the vessels. The optical measurement section 33 is disposed at a predetermined position with respect to the measurement cell 31. The optical measurement cell 33 rediates an exciting light to the slab-type optical waveguide 11 at a predetermined angle, and detects a signal light which is output from the slab-type optical waveguide 11 at another predetermined angle so that a degree of immunity reaction is detected. The instruction section 34 receives instruction from a user. The data section 35 holds predetermined data corresponding to a condition such as an object for inspection, a measurement item, a measurement number and the like. The pouring control section 36 controls sucking, discharging, a quantity of sucking, and a quantity of discharging of the pouring nozzle 32a based upon information from the instruction section 34 and the data section 35. The main control section 37 sends commands to the optical measurement section 33 and the pouring control section 36.

In this optical measurement apparatus, the main control section 37 reads out corresponding data from the data section 35, operates the pouring control section 36 based upon the read out data and the user's instruction, and controls the pouring nozzle 32a, in correspondence to each step in the flowchart illustrated in FIG. 9. That is, the test liquid for measurement is sucked from the test liquid housing vessel by the pouring nozzle 32a, the pouring nozzle 32a is moved to the reaction vessel 12, and then the sucked test liquid for measurement is discharged into the reaction vessel 12 so that the antigen-antibody reaction for the first stage is carried out. When the test liquid for measurement is to be diluted, the dilution liquid is sucked from the dilution liquid housing vessel prior to or after the sucking of the test liquid for measurement. Thereafter, the test liquid for measurement within the reaction vessel 12 is sucked by the pouring nozzle 32a and is discharged to a waste liquid tank (not illustrated). Then, a reagent which includes labeled antibodies 18 and fine grains of carbon black 19, is sucked from the reagent housing vessel by the pouring nozzle 32a, the pouring nozzle 32a is moved to the reaction vessel 12, and then the sucked reagent is discharged into the reaction vessel 12 so that the antigen-antibody reaction for the second stage is carried out. In these cases, adjusting of the quantity of sucked liquid is performed, for example, by determining a pulse number per a unit time to be the most optimum value which corresponds to the sucking quantity, by the pouring control section 36. The pulse number is supplied to a pulse motor (not illustrated) which controls the sucking quantity and the discharging quantity of the pouring nozzle 32a. Further, it is possible that the reagent and the test liquid for measurement are sucked in this order and the reagent and the test liquid for measurement are discharged in this order. In this case, both liquids are prevented from mixing within the pouring nozzle 32a by forming an air gap between the reagent and the test liquid for measurement.

Therefore, the absorbance substance is securely included within the reaction vessel 2, 12 when the optical immunity measurement i s carried out. As is apparent from the foregoing embodiments, the reagent stray light is sufficiently reduced so that the sensitivity (S/N ratio) of the optical immunity measurement is remarkably improved.

In this embodiment, a so-called 2 step method is employed which carries out the antigen-antibody reaction for the first stage by pouring the test liquid for measurement into the reaction vessel 2, 12, and then carries out the antigen-antibody reaction for the second stage by pouring the reagent after the test liquid has been discharged. It is possible that a so-called 1 step sandwich method is employed which carries out the antigen-antibody reaction by previously mixing the test liquid and the reagent, and carries out the antigen-antibody reaction between the antibodies 3, 13 fixed on the surface of the slab-type optical waveguide 1, 11 and the already reacted antigens by pouring the mixed liquid into the reaction vessel 2, 12.

Further, any of the above embodiments describes the case where the absorbance substance is previously included in the reagent. It is possible that the absorbant substance is poured into the reaction vessel prior to or after pouring of the reagent.

Possibility In Industrial Utilization

The present invention is preferably applied to a measurement apparatus which forms a reaction vessel in one body with a slab-type optical waveguide, and which apparatus measures the optical characteristics in the vicinity of a surface of the slab-type optical waveguide by pouring a test liquid for measurement and a reagent into the reaction vessel and by introducing an exciting light into the slab-type optical waveguide. An S/N ratio of the optical measurement is improved.

What is claimed is:

1. An optical measurement apparatus comprising:
   a reaction vessel for holding liquids;
   an optical waveguide for propagating light therewithin, the optical waveguide forming at least one surface of the reaction vessel wherein a substance is fixed on the surface for binding to a substance to be measured;
   means for radiating an exciting light to the optical waveguide at a first predetermined angle relative to the optical waveguide;
   a fluorescent substance which produces fluorescent light when excited by the exciting light contained within the reaction vessel for labeling at least a portion of a substance to be measured which is bound to the substance fixed on the surface of the waveguide;

a light absorbing material contained within the reaction vessel, the light absorbing material absorbing light at a wavelength of the exciting light or at a wavelength of the fluorescent light; and means for measuring fluorescent light which is emitted from the fluorescent substance labeling a portion of a substance to be measured which is bound to the substance fixed on the surface of the waveguide at a second predetermined angle relative to the optical waveguide.

2. An optical measurement apparatus as recited in claim 1 wherein the first predetermined angle and the second predetermined angle are the same.

3. An optical measurement apparatus as recited in claim 1, wherein the light absorbing material is a water soluble dye.

4. An optical measurement apparatus as recited in claim 1, wherein the light absorbing material is fine grains of material.

5. An optical measurement apparatus as recited in claim 4, wherein the light absorbing material is fine grains of material selected from the group consisting of carbon black, metal, polystyrene and polyethylene.

6. An optical measurement apparatus as recited in claim 5, wherein the light absorbing material is fine grains of platinum or gold.

7. An optical measurement apparatus as recited in claim 4, wherein the fine grains of material have a diameter of about 200 nm.

8. An optical measurement apparatus as recited in claim 4, wherein a concentration of the fine grains of material in the reaction vessel ranges from 0.004%–0.3%.

9. An optical measurement apparatus as recited in claim 1, wherein the fluorescent light propagates within the waveguide in a totally reflective manner.

10. An optical measurement apparatus as recited in claim 1, wherein each of the fluorescently labeled substance, the substance to be measured and the substance fixed to the surface of the optical waveguide is a ligand.

11. The optical measurement method as recited in claim 10, wherein each of the fluorescently labeled substance, the substance to be measured and the substance fixed to the surface of the optical waveguide is an antigen or an antibody.

12. An optical measurement apparatus as recited in claim 1, wherein the light absorbing material absorbs light at a wavelength of the exciting light and at a wavelength of the fluorescent light.

13. An optical measurement apparatus as recited in claim 1, wherein the first and second predetermined angles are parallel to a length of the waveguide.

14. An optical measurement apparatus as recited in claim 1, wherein the first predetermined angle is perpendicular to a length of the waveguide, and the second predetermined angle is parallel to the length of the waveguide.

15. An optical measurement apparatus as recited in claim 1, wherein the exciting light is transmitted to the waveguide through a collimator and a neutral density filter.

16. An optical concentration measurement method comprising;

pouring a test liquid containing a substance to be measured into a reaction vessel and pouring a reagent liquid containing a fluorescent substance, which fluorescent substance produces fluorescent light when excited by an exciting light, into the reaction vessel, such that at least a portion of the substance to be measured binds to a substance fixed to a surface of an optical waveguide which forms a wall of the reaction vessel, and at least a portion of the fluorescent substance binds to the at least a portion of the substance to be measured bound to the substance fixed to the surface of the optical waveguide, so as to constrain the at least a portion of the substance to be measured and the at least a portion of the fluorescent substance in a vicinity of the optical waveguide, adding a light absorbing material to the reaction vessel, which light absorbing material absorbs light at an exciting wavelength of the fluorescent substance or at an emitting wavelength of the fluorescent substance, introducing an exciting light into the optical waveguide at a first predetermined angle relative to the optical waveguide for exciting the at least a portion of the fluorescent substance constrained in the vicinity of the surface of the optical waveguide, whereby the at least a portion of the fluorescent substance constrained in the vicinity of the surface of the optical waveguide is excited by the exciting light into emitting fluorescent light, measuring the emitted fluorescent light which is output from the waveguide at a second predetermined angle relative to the optical waveguide, determining the concentration of the substance to be measured from the measurement of the emitted fluorescent light.

17. An optical measurement methods as recited in claim 16, wherein the first predetermined angle and the second predetermined angle are the same.

18. The optical measurement method as recited in claim 17, wherein the first and second predetermined angles are parallel to a length of the waveguide.

19. The optical measurement method as recited in claim 16, wherein the light absorbing material is a water soluble dye.

20. The optical measurement method as recited in claim 16, wherein the light absorbing material is fine grains of material.

21. The optical measurement method as recited in claim 20, wherein the light absorbing material is fine grains of material selected from the group consisting of carbon black, metal, polystyrene and polyethylene.

22. The optical measurement method as recited in claim 21, wherein the light absorbing material is fine grains of platinum or gold.

23. The optical measurement method as recited in claim 20, wherein the fine grains of material have a diameter of about 200 nm.

24. The optical measurement method as recited in claim 20, wherein a concentration of the fine grains of material in the reaction vessel ranges from 0.004%–0.3%.

25. The optical measurement method as recited in claim 16, wherein the fluorescent light propagates within the waveguide in a totally reflective manner.

26. The optical measurement method as recited in claim 16, wherein the light absorbing material absorbs light at a wavelength of the exciting light and at a wavelength of the fluorescent light.

27. The optical measurement method as recited in claim 16, wherein the exciting light is transmitted to the waveguide through a collimator and a neutral density filter.

28. The optical measurement method as recited in claim 16, wherein the first predetermined angle is perpendicular to a length of the waveguide, and the second predetermined angle is parallel to the length of the waveguide.

29. The optical measurement method as recited in claim 16, wherein each of the fluorescently labeled substance, the substance to be measured and the substance fixed to the surface of the optical waveguide is a ligand.

30. The optical measurement method as recited in claim 29, wherein each of the fluorescently labeled substance, the substance to be measured and the substance fixed to the surface of the optical waveguide is an antigen or an antibody.

31. An optical concentration measurement method comprising:

providing a substance fixed to a surface of an optical waveguide which forms a wall of a reaction vessel, pouring a test liquid containing a substance to be measured into the reaction vessel, the substance to be measured being labeled with a fluorescent label which produces fluorescent light when excited by an exciting light, such that at least a portion of the substance to be measured binds to the substance fixed to the surface of the optical waveguide so as to constrain the at least a portion of the substance to be measured to the in a vicinity of the optical waveguide, adding a light absorbing material to the reaction vessel, which light absorbing material absorbs light at an exciting wavelength of the fluorescent label or at an emitting wavelength of the fluorescent label, introducing an exciting light into the optical waveguide at a first predetermined angle relative to the optical waveguide, for exciting the fluorescent label of the at least a portion of the substance to be measured constrained in the vicinity of the surface of the optical waveguide, whereby the fluorescent label of the at least a portion of the substance to be measured constrained at the surface of the optical waveguide is excited by the exciting light into emitting fluorescent light, measuring the emitted fluorescent light which is output from the waveguide at a second predetermined angle relative to the optical waveguide, determining the concentration of the substance to be measured from the measurement of the emitted fluorescent light.

32. The optical measurement method as recited in claim 31, wherein the light absorbing material is a water soluble dye.

33. The optical measurement method as recited in claim 31, wherein the light absorbing material is fine grains of material.

34. The optical measurement method as recited in claim 33, wherein the fine grains of material have a diameter of about 200 nm.

35. The optical measurement method as recited in claim 33, wherein a concentration of the fine grains of material in the reaction vessel ranges from 0.004%–0.3%.

36. The optical measurement method as recited in claim 31, wherein the light absorbing material is fine grains of material selected from the group consisting of carbon black, metal, polystyrene and polyethylene.

37. The optical measurement method as recited in claim 36, wherein the light absorbing material is fine grains of platinum or gold.

38. The optical measurement method as recited in claim 31, wherein the light absorbing material absorbs light at a wavelength of the exciting light and at a wavelength of the fluorescent light.

39. The optical measurement method as recited in claim 31, wherein the fluorescent light propagates within the waveguide in a totally reflective manner.

40. An optical measurement method as recited in claim 31, wherein the first predetermined angle and the second predetermined angle are the same.

41. The optical measurement method as recited in claim 40, wherein the first and second predetermined angles are parallel to a length of the waveguide.

42. The optical measurement method as recited in claim 31, wherein the first predetermined angle is perpendicular to a length of the waveguide, and the second predetermined angle is parallel to the length of the waveguide.

43. The optical measurement method as recited in claim 31, wherein the exciting light is transmitted to the waveguide through a collimator and a neutral density filter.

44. The optical measurement method as recited in claim 31, wherein each of the substance to be measured and the substance fixed to the surface of the optical waveguide is a ligand.

45. The optical measurement method as recited in claim 44, wherein each of the substance to be measured and the substance fixed to the surface of the optical waveguide is an antigen or an antibody.

* * * * *